(12) United States Patent
Whitham

(10) Patent No.: US 6,366,641 B1
(45) Date of Patent: Apr. 2, 2002

(54) REDUCING DARK CURRENT IN A STANDING WAVE LINEAR ACCELERATOR

(75) Inventor: Kenneth Whitham, Alamo, CA (US)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 0 days.

(21) Appl. No.: 09/865,375

(22) Filed: May 25, 2001

(51) Int. Cl.[7] .............................................. A61N 5/10
(52) U.S. Cl. ...................... 378/65; 378/116; 250/505.1; 250/492.3; 315/5.41; 315/500; 315/505
(58) Field of Search ................. 378/65, 116; 250/492.3, 250/505.1; 315/505

(56) References Cited

U.S. PATENT DOCUMENTS

| | | | |
|---|---|---|---|
| 3,581,145 A | 5/1971 | Morris | 315/30 |
| 3,965,434 A | 6/1976 | Helgesson | 315/500 |
| 4,107,617 A | 8/1978 | Tran | 315/500 |
| 4,627,089 A | 12/1986 | Menor et al. | 378/157 |
| 4,726,046 A | 2/1988 | Nunan | 378/65 |
| 4,737,647 A | 4/1988 | Stieber | 250/505.1 |
| 4,868,843 A | 9/1989 | Nunan | 378/152 |
| 4,901,336 A | 2/1990 | Nishiki | 378/98.8 |
| 5,216,255 A * | 6/1993 | Weidlich | 250/492.3 |
| 5,332,908 A * | 7/1994 | Weidlich | 250/492.1 |
| 5,449,916 A | 9/1995 | Smyth et al. | 250/398 |
| 5,452,338 A | 9/1995 | Granfors et al. | 378/98.11 |
| 5,604,781 A | 2/1997 | Suzuki et al. | 378/62 |
| 5,789,876 A * | 8/1998 | Umstadter et al. | 315/507 |

* cited by examiner

Primary Examiner—Robert H. Kim
Assistant Examiner—Jurie Yun

(57) ABSTRACT

Systems and methods for reducing dark current levels in a standing wave linear accelerator without sacrificing operating performance are described. In a radiation mode, the standing wave linear accelerator is operated to produce a pulsed therapeutic photon beam having a characteristic pulse width. In an electron mode, the standing wave linear accelerator is operated to produce a pulsed therapeutic electron beam having a characteristic pulse width that is shorter than the characteristic pulse width of the therapeutic photon beam. In some embodiments, assuming a uniform dark current level, the dark current level may be reduced in proportion with the beam pulse width reduction in the electron mode of operation. A system for implementing this therapeutic beam generation method also is described.

20 Claims, 4 Drawing Sheets

REDUCING DARK CURRENT IN A STANDING WAVE LINEAR ACCELERATOR

TECHNICAL FIELD

This invention relates to systems and methods of reducing dark current levels in a standing wave linear accelerator.

BACKGROUND

Radiation therapy involves delivering a high, curative dose of radiation to a tumor, while minimizing the dose delivered to surrounding healthy tissues and adjacent healthy organs. Therapeutic radiation doses may be supplied by a standing wave linear accelerator that is configured to generate a high-energy (e.g., several MeV) electron beam. In an electron mode of operation, the electron beam may be applied directly to one or more therapy sites on a patient. Alternatively, in a radiation mode of operation, the electron beam may be used to generate a photon (e.g., X-ray) beam that may be applied to the patient. The shape of the radiation beam at the therapy site may be controlled by discrete collimators of various shapes and sizes or by multiple leaves (or finger projections) of a multi-leaf collimator that are positioned to block selected portions of the radiation beam. The multiple leaves may be programmed to contain the radiation beam within the boundaries of the therapy site and, thereby, prevent healthy tissues and organs that are located beyond the boundaries of the therapy site from being exposed to the radiation beam.

In general, a standing wave linear accelerator includes a particle source (e.g., an electron gun) that directs charged particles (e.g., electrons) into an accelerating cavity. The charged particles travel through a succession of accelerating cavities, where the particles are focused and accelerated by an electromagnetic (RF) field that is applied by an external RF source (e.g., a klystron or a magnetron). Additional electrons may be introduced into the standing wave linear accelerator by sources other than the cathode of the electron gun. These additional electrons are accelerated in the linear accelerator to produce an undesirable background "dark current". As used herein, "dark current" refers to the electron beam current that is produced by an accelerator system when the electron gun is turned off and the RF source is turned on. Among the sources of dark current in standing wave linear accelerators is the electron gun itself. When the electron gun is hot (i.e., the filament is on and the gun is warmed up), the cathode will emit electrons in the presence of an accelerating voltage. When the gun is off, electrons also may be emitted from the grid structure that is used to bias the gun off. The first half cavity in the standing wave linear accelerator is another source of dark current. In particular, over time, this cavity may become coated with oxides that are produced by the gun cathode, especially when the gun is run above rated current levels. These oxide coatings reduce the work function of the cavity surfaces such that a low current electron beam may be produced in the presence of high electric fields, even if the cavity surfaces are cool.

Dark current introduces undesirable beam that reduces the ability to measure and control the therapeutic beams produced by standing wave linear accelerators. In addition, the background dark current beam may interfere with the associated imaging system and, consequently, may result in a poor or inaccurate diagnosis of a patient.

SUMMARY

The invention features systems and methods for reducing dark current levels in a standing wave linear accelerator without sacrificing operating performance.

In one aspect, the invention features a method of generating a therapeutic beam. In a radiation mode, a standing wave linear accelerator is operated to produce a pulsed therapeutic photon beam having a characteristic pulse width. In an electron mode, the standing wave linear accelerator is operated to produce a pulsed therapeutic electron beam having a characteristic pulse width that is shorter than the characteristic pulse width of the therapeutic photon beam.

In some embodiments, assuming a uniform dark current level, the dark current level may be reduced in proportion with the beam pulse width reduction in the electron mode of operation.

Embodiments in accordance with this aspect of the invention may include one or more of the following features.

The therapeutic photon beam and the therapeutic electron beam preferably have substantially the same pulse repetition rate.

The therapeutic photon beam may be produced by intercepting a pulsed electron source beam with an x-ray target. The electron source beam typically has a lower beam current than the therapeutic electron beam.

The pulse width of the therapeutic photon beam may correspond to a factory-preset pulse width. The pulse width of the therapeutic electron beam may be adjusted to reduce dark current produced by the standing wave linear accelerator. The pulse width of the therapeutic electron beam may be adjusted to substantially correspond to a characteristic fill time for the standing wave linear accelerator.

The therapeutic electron beam current level may be adjusted to accommodate adjustment of the pulse width of the therapeutic electron beam. The electron beam current level may be adjusted proportionately with the pulse width adjustment to maintain a desired dosage level.

In one embodiment, the therapeutic photon beam has an energy level of about 1 MeV or greater, and the therapeutic electron beam has an energy level of about 4–24 MeV.

In another aspect, the invention features a system for implementing the above-described therapeutic beam generation method.

Other features and advantages of the invention will become apparent from the following description, including the drawings and the claims.

DETAILED DESCRIPTION

In the following description, like reference numbers are used to identify like elements. Furthermore, the drawings are intended to illustrate major features of exemplary embodiments in a diagrammatic manner. The drawings are not intended to depict every feature of actual embodiments nor relative dimensions of the depicted elements, and are not drawn to scale.

Figure 1:
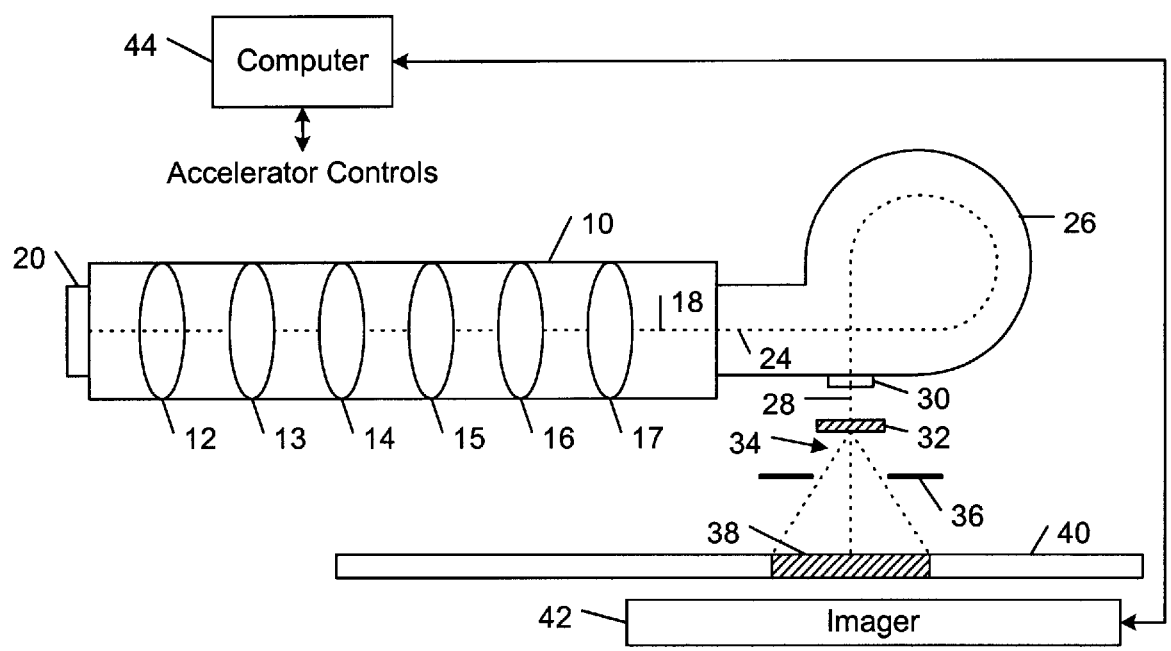
FIG. 1 is a block diagram of a radiation treatment device delivering a therapeutic radiation beam to a therapy site on a patient.

Referring to FIG. 1, in one embodiment, a standing wave charged particle linear accelerator 10 for use in a medical radiotherapy device includes a series of accelerating cavities 12, 13, 14, 15, 16, 17 that are aligned along a beam axis 18. A particle source 20 (e.g., an electron gun) directs charged particles (e.g., electrons) into the first accelerating cavity 12. As the charged particles travel through the succession of accelerating cavities 12–17, the particles are focused and accelerated by an electromagnetic field that is applied by an external source (e.g., a magnetron or a klystron amplifier). The resulting accelerated particle beam 24 may be directed to a magnetic energy filter 26 that bends beam 24 by approximately 270°. A filtered output beam 28 is directed through a window 30 to a target 32 that generates an x-ray beam 34. The intensity of radiation beam 34 typically is constant. One or more adjustable leaves 36 may be positioned to block selected portions of radiation beam 34 to conform the boundary of radiation beam 34 to the boundaries of a therapy site 38 on a patient 40. An imager 42 collects image data corresponding to the intensity of radiation passing through patient 40. A computer 44 typically is programmed to control the operation of leaves 36 to generate a prescribed intensity profile over the course of a treatment, and to control the operation of linear accelerator 10 and imager 42.

Figure 2:
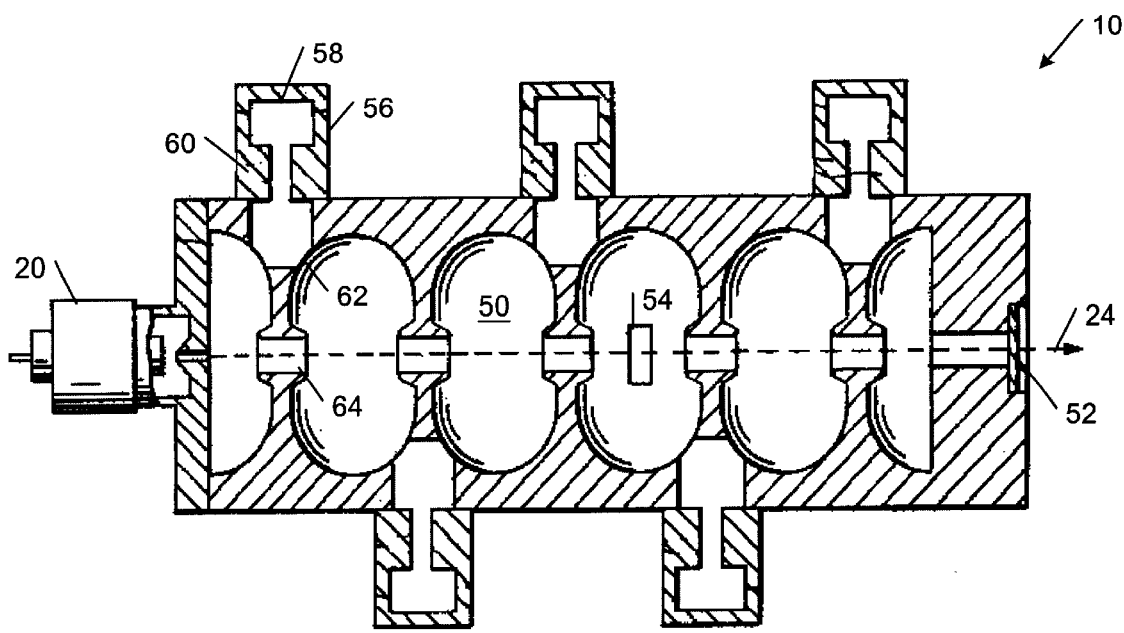
FIG. 2 is a diagrammatic cross-sectional side view of a side cavity coupled standing wave linear accelerator.

Referring to FIG. 2, in one embodiment, linear accelerator 10 is implemented as a coupled cavity accelerator (e.g., a coupled cavity linear accelerator or a coupled cavity drift tube linear accelerator). In this embodiment, linear accelerator 10 includes a plurality of accelerating cavity resonators 50 that are arranged successively along beam axis 18 and are configured to accelerate charged particles within beam 24 to nearly the velocity of light. Particle source 20 forms and injects a beam of charged particles into linear accelerator 10. An output window 52, which is disposed at the downstream end of linear accelerator 10, is permeable to the high energy particle beam 24, but is impermeable to gas molecules. Linear accelerator 10 and particle source 20 typically are evacuated to a suitably low pressure (e.g., $10^{-6}$ torr) by a vacuum pump (not shown).

Linear accelerator 10 is excited with microwave energy produced by a conventional microwave source (e.g., a magnetron or a klystron amplifier) that may be connected to linear accelerator 10 by a waveguide, which may be coupled to one of the accelerating cavity resonators 50 by an inlet iris 54. The microwave source may be configured for S-band operation and the cavity resonators 50 may be configured to be resonant at S-band. In operation, the resonant microwave fields in linear accelerator 10 electromagnetically interact with the charged particles of beam 24 to accelerate the particles essentially to the velocity of light at the downstream end of linear accelerator 10. As described above, the resulting charged particle beam 24 may bombard an x-ray target to produce high energy x-rays, or may be used to irradiate patient 40 or another object directly.

A plurality of coupling cavities 56 are disposed off beam axis 18 and are configured to couple adjacent accelerating cavities 50 electromagnetically. Each coupling cavity 56 includes a cylindrical sidewall 58 and a pair of centrally disposed inwardly projecting capacitive loading members 60 that project into and capacitively load the coupling cavity 56. Each coupling cavity 56 is disposed tangentially to the accelerating cavities 50. The corners of each coupling cavity 56 intersect the inside walls of a pair of adjacent accelerating cavities 50 to define magnetic field coupling irises 62, which provide electromagnetic wave energy coupling between the accelerating cavities 50 and the associated coupling cavities 56. The accelerating cavities 50 and the coupling cavities 56 are tuned substantially to the same frequency.

Figure 3:
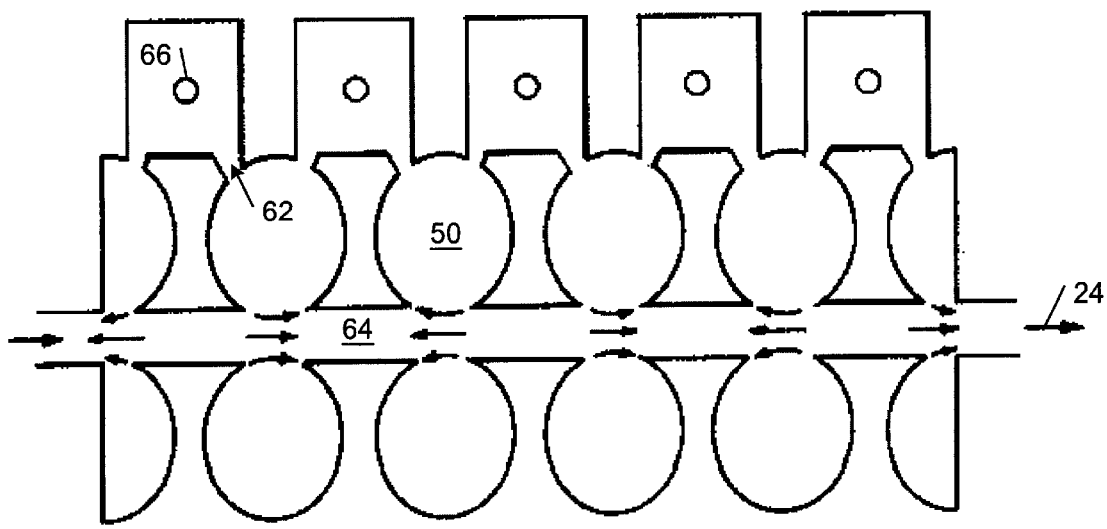
FIG. 3 is a diagrammatic representation of electric field orientation in the standing wave linear accelerator of FIG. 2 operated in a π/2 resonance mode at one instant of maximum electric field.

As shown in FIG. 3, in one mode of operation, the gaps 64 between accelerating cavities 50 are spaced so that charged particles travel from one gap to the next in ½ rf cycle of the microwave source. As a result, after experiencing an accelerating field in one gap, the charged particles arrive at the next gap when the direction of the field in the next gap has reversed direction to further accelerate the charged particles. The field in each side cavity 56 is advanced in phase by $\pi/2$ radians from the preceding accelerating cavity 50 so that the complete resonant structure of linear accelerator 10 operates in a mode with $\pi/2$ phase shift per cavity (i.e., a $\pi/2$ resonance mode). Since charged particle beam 24 does not interact with side cavities 56, charged particle beam 24 experiences the equivalent acceleration of a structure with a $\pi$-radian phase shift between adjacent accelerating cavities 50. In this embodiment, the essentially standing wave pattern within linear accelerator has very small fields 66 in side cavities 56 because the end cavities also are configured as accelerating cavities 50. This feature minimizes rf losses in the non-working side cavities 56. In addition, configuring the end cavities as half cavities improves the charged particle beam entrance conditions and provides a symmetrical resonant structure with uniform fields in each accelerating cavity 50. In one embodiment, the microwave source may provide sufficient energy for linear accelerator 10 to produce a charged particle beam 24 with a maximum output energy in the range of about 4 MeV to about 24 MeV, while operating in a $\pi/2$ resonance mode.

Linear accelerator 10 also may be operated in a number of different, non-$\pi/2$ resonance (or standing wave) modes.

As mentioned above, the operating parameters of linear accelerator 10 may be adjusted to reduce dark current levels without sacrificing operating performance. In particular, dark current levels may be reduced by reducing the pulse width of the accelerator beam. Assuming a uniform dark current level, any reduction in the beam pulse width will reduce the dark current level produced at the output of linear accelerator 10 by a proportionate amount. For example, if the pulse width were reduced from 4 µs to 0.4 µs, the dark current level in linear accelerator 10 would be reduced by a factor of ten. Typically, the beam current level is increased in proportion with the beam pulse width reduction to maintain the same dosage rate.

Figure 4:
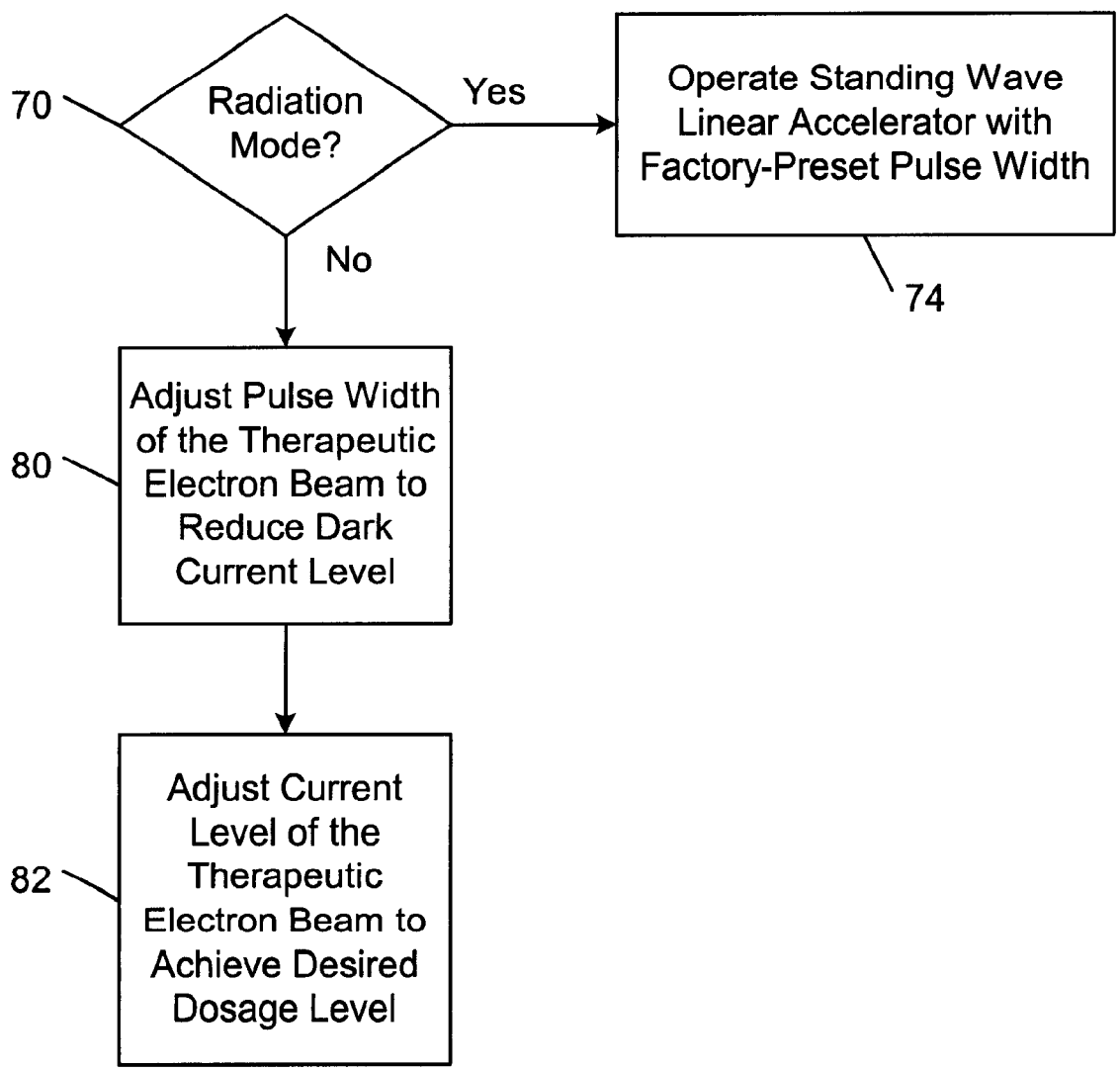
FIG. 4 is a flow diagram of a method of generating a therapeutic beam with the standing wave linear accelerator of FIG. 2.
Figure 5A:
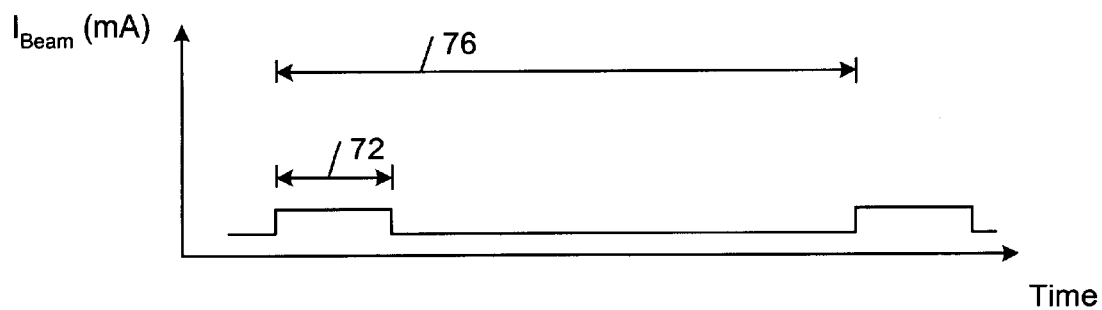
FIG. 5A is a graphical representation of electron beam current in the standing wave linear accelerator of FIG. 2 operating in a radiation mode plotted as a function of time.
Figure 5B:
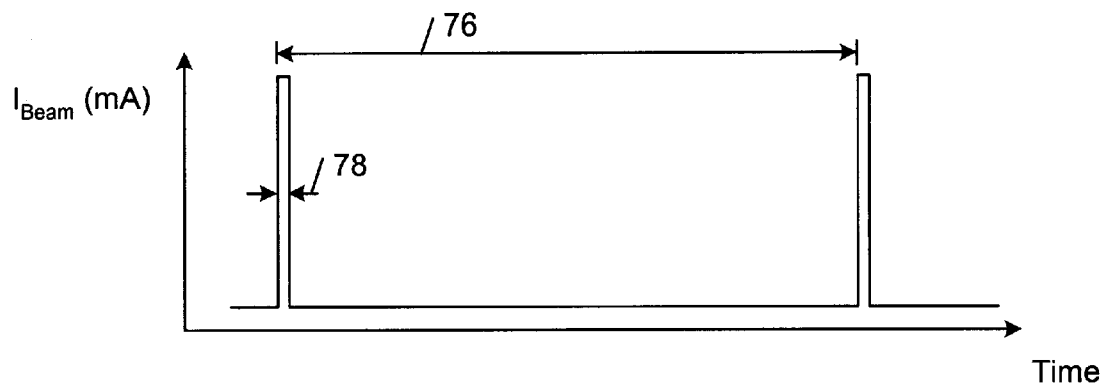
FIG. 5B is a graphical representation of electron beam current in the standing wave linear accelerator of FIG. 2 operating in an electron mode plotted as a function of time.

Referring to FIGS. 4, 5A and 5B, in one embodiment, dark current levels in linear accelerator 10 may be reduced as follows.

As shown in FIG. 5A, in the radiation mode (step 70), standing wave linear accelerator 10 is operated with a factory-preset pulse width 72 (step 74). The factory preset pulse width 72 may be on the order of about 4 µs and the pulse period 76 may be on the order of about 2 ms. In one embodiment, linear accelerator 10 is operated in a $\pi/2$ resonance mode to produce a source charged particle beam 28. The source charged particle beam 28 may have an output energy level that is between about 4 MeV and about 24 MeV.

The source charged particle beam 28 may be intercepted by target 32 to produce a therapeutic radiation beam 34. Target 32 may be a conventional x-ray target that includes an energy filter or an energy absorber that is configured to tailor the energy level of therapeutic radiation beam 34 to a desired level (e.g., on the order of about 1 MeV or greater). For example, target 32 may include a high-Z material (e.g., a material with an atomic number of seventy-two or greater, such as tungsten, tantalum, gold and alloys thereof) that produces x-ray radiation that contains essentially no low-energy x-rays. If necessary, the energy level of therapeutic radiation beam 34 may be tailored further by raising or lowering the rf energy level supplied by the microwave source. The input charged particle beam injection current also may be adjusted to tailor the characteristics of therapeutic radiation beam 34. The resulting therapeutic radiation beam 34 may be delivered to patient 40 for treatment purposes.

As shown in FIG. 5B, in the electron mode (step 70), the pulse width 78 of the therapeutic electron beam 28 produced by standing wave linear accelerator 10 is adjusted to reduce the dark current level in the system (step 80). As explained above, assuming a uniform dark current level, any reduction in the RF pulse width 78 will reduce the dark current level produced at the output of linear accelerator 10 by a proportionate amount. In one embodiment, linear accelerator 10 is operated in a $\pi/2$ resonance mode to produce a therapeutic charged particle beam 28. The therapeutic charged particle beam 28 may have a pulse width 78 that is on the order of about 0.4 $\mu$s, a pulse period 76 that is on the order of about 2 ms, and an output energy level that is between about 4 MeV and about 24 MeV. The beam current level also is adjusted proportionately to maintain the same dosage rate (step 82). As a result, undesirable dark current levels in linear accelerator 10 may be reduced substantially without changing the prescribed therapeutic treatment protocol.

The pulse width of therapeutic electron beam 28 may be adjusted in a variety of different ways that depend, at least in part, upon the particular implementation of the external rf source. For example, in embodiments that include an external klystron amplifier rf source, the beam pulse width may be adjusted by shifting the phase of the klystron rf driver pulse relative to the klystron input voltage pulse.

Figure 6:
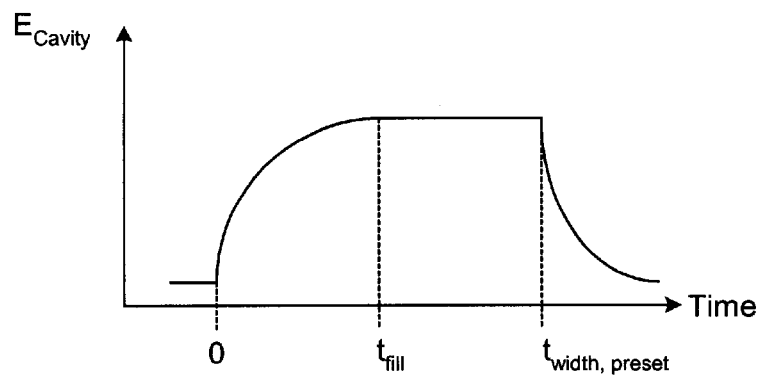
FIG. 6 is a graphical representation of electric field strength in the standing wave accelerator of FIG. 2 plotted as a function of time.

Referring to FIG. 6, in some embodiments, the pulse width 78 of the therapeutic electron beam 28 produced by standing wave linear accelerator 10 may be reduced from the factory-preset pulse width 78 ($t_{width,\ preset}$) down to approximately the characteristic fill-time ($t_{fill}$) of standing wave linear accelerator 10. The fill time ($t_{fill}$) corresponds to the amount of time needed for the electric fields to build-up within accelerating cavities 12–17 after an rf pulse is applied from the external rf source. The fill time depends upon a number of parameters, including the design of linear accelerator 10 and the particular operating conditions. Typically, the fill time of most commercial linear accelerators under normal operating conditions is on the order of 0.2–1 $\mu$s. Of course, the minimum width of beam pulse 78 may be limited by the maximum beam current of linear accelerator 10 and the dosage requirements prescribed for a particular patient treatment protocol.

Other embodiments are within the scope of the claims.

For example, dark current levels also may be reduced in the radiation mode of operation by reducing the beam pulse width relative to the factory-preset pulse width. The impact of such a dark current reduction, however, is less significant than a corresponding dark current reduction in the electron mode because dark current represents a substantially smaller fraction of the total beam current in the radiation mode of operation.

In addition, although the above embodiments are described in connection with side coupling cavities, other forms of energy coupling (e.g., coupling cavities pancaked between accelerating cavities 50) may be used.

Still other embodiments are within the scope of the claims.

What is claimed is:

1. A method of generating a therapeutic beam, comprising:
   operating a standing wave linear accelerator in a radiation mode to produce a pulsed therapeutic photon beam having a characteristic pulse width; and
   operating the standing wave linear accelerator in an electron mode to produce a pulsed therapeutic electron beam having a characteristic pulse width that is shorter than the characteristic pulse width of the therapeutic photon beam.

2. The method of claim 1, wherein the therapeutic photon beam and the therapeutic electron beam have substantially the same pulse repetition rate.

3. The method of claim 1, wherein the therapeutic photon beam is produced by intercepting a pulsed electron source beam with an x-ray target.

4. The method of claim 3, wherein the electron source beam has a lower beam current than the therapeutic electron beam.

5. The method of claim 1, wherein the pulse width of the therapeutic photon beam corresponds to a factory-preset pulse width.

6. The method of claim 1, wherein the pulse width of the therapeutic electron beam substantially corresponds to a characteristic fill time for the standing wave linear accelerator.

7. The method of claim 1, further comprising adjusting the pulse width of the therapeutic electron beam to reduce dark current produced by the standing wave linear accelerator.

8. The method of claim 7, further comprising adjusting the therapeutic electron beam current level to accommodate adjustment of the pulse width of the therapeutic electron beam.

9. The method of claim 8, wherein the electron beam current level is adjusted proportionately with the pulse width adjustment to maintain a desired dosage level.

10. The method of claim 1, wherein the therapeutic photon beam has an energy level of about 1 MeV or greater, and the therapeutic electron beam has an energy level of about 4–24 MeV.

11. A system for generating a therapeutic beam, comprising:
    a standing wave linear accelerator; and
    a controller configured to
        operate the standing wave linear accelerator in a radiation mode to produce a pulsed therapeutic photon beam having a characteristic pulse width; and
        operate the standing wave linear accelerator in an electron mode to produce a pulsed therapeutic electron beam having a characteristic pulse width that is shorter than the characteristic pulse width of the therapeutic photon beam.

12. The system of claim 11, wherein the therapeutic photon beam and the therapeutic electron beam have substantially the same pulse repetition rate.

13. The system of claim 11, wherein the therapeutic photon beam is produced by intercepting a pulsed electron source beam with an x-ray target.

14. The system of claim 13, wherein the electron source beam has a lower beam current than the therapeutic electron beam.

15. The system of claim 11, wherein the pulse width of the therapeutic photon beam corresponds to a factory-preset pulse width.

16. The system of claim 11, wherein the pulse width of the therapeutic electron beam substantially corresponds to a characteristic fill time for the standing wave linear accelerator.

17. The system of claim 11, wherein the controller is configured to enable the pulse width of the therapeutic electron beam to be adjusted to reduce dark current produced by the standing wave linear accelerator.

18. The system of claim 17, wherein the controller is configured to enable the therapeutic electron beam current level to be adjusted to accommodate adjustment of the pulse width of the therapeutic electron beam.

19. The system of claim 18, wherein the electron beam current level is adjusted proportionately with the pulse width adjustment to maintain a desired dosage level.

20. The system of claim 11, wherein the therapeutic photon beam has an energy level of about 1 MeV or greater, and the therapeutic electron beam has an energy level of about 4–24 MeV.

* * * * *